US012670407B2

(12) United States Patent
Louisell, III et al.

(10) Patent No.: US 12,670,407 B2
(45) Date of Patent: Jun. 30, 2026

(54) SYSTEMS AND METHODS FOR FORECASTING OPERATIONAL AND STRATEGIC IMPACTS OF CLIMATE CHANGE ON WATER QUALITY AND/OR QUANTITY

(71) Applicant: True Elements, Inc., Naples, FL (US)

(72) Inventors: William C. Louisell, III, Mt. Pleasant, SC (US); David Bankston, Naples, FL (US)

(73) Assignee: True Elements, Inc., Naples, FL (US)

( * ) Notice: Subject to any disclaimer, the term of this patent is extended or adjusted under 35 U.S.C. 154(b) by 711 days.

(21) Appl. No.: 18/156,241

(22) Filed: Jan. 18, 2023

(65) Prior Publication Data

US 2023/0229928 A1     Jul. 20, 2023

Related U.S. Application Data

(60) Provisional application No. 63/300,756, filed on Jan. 19, 2022, provisional application No. 63/421,824, filed on Nov. 2, 2022.

(51) Int. Cl.
| | |
|---|---|
| *G06N 3/09* | (2023.01) |
| *G06N 3/082* | (2023.01) |
| *G01N 33/18* | (2006.01) |
| *G06F 16/29* | (2019.01) |
| *G06N 7/01* | (2023.01) |

(52) U.S. Cl.
CPC .............. *G06N 3/09* (2023.01); *G06N 3/082* (2013.01); *G01N 33/18* (2013.01); *G06F 16/29* (2019.01); *G06N 7/01* (2023.01)

(58) Field of Classification Search
USPC .......................................................... 702/2
See application file for complete search history.

(56) References Cited

U.S. PATENT DOCUMENTS

| | | | | |
|---|---|---|---|---|
| 5,646,863 | A * | 7/1997 | Morton .................. | G01N 33/18 |
| | | | | 210/85 |
| 2015/0241403 | A1* | 8/2015 | Nelson .................. | G06Q 10/067 |
| | | | | 702/2 |
| 2021/0029866 | A1* | 2/2021 | Placella ................. | G06Q 10/04 |
| 2021/0256378 | A1* | 8/2021 | Watt ....................... | G06N 3/044 |
| 2023/0060380 | A1* | 3/2023 | Singh .................... | G06F 16/215 |
| 2023/0068107 | A1* | 3/2023 | De Jong ................ | G06Q 40/08 |

* cited by examiner

*Primary Examiner* — Paul D Lee
(74) *Attorney, Agent, or Firm* — Michele V. Frank; Venable LLP

(57)     ABSTRACT

Systems, methods, and computer-readable storage media for forecasting the impact of climate change, and more specifically to the impact on water quality and/or quantity. The system receives, from a plurality of sensors within a predefined geographic area, environmental data. The system normalizes the environmental data and executes an artificial intelligence algorithm, where inputs to the artificial intelligence algorithm include the normalized environmental data, and outputs of the artificial intelligence algorithm include environmental risks, consequences, and probabilities associated with at least one environmental event. The system then modifies a planned project using the environmental risks, consequences, and probabilities associated with the at least one environmental event.

17 Claims, 7 Drawing Sheets

Start

902 — Receiving, at a computer system from a plurality of sensors within a predefined geographic area, environmental data 904 — Normalizing, via at least one processor of the computer system, the environmental data, resulting in normalized environmental data 906 — Executing, via the at least one processor, an artificial intelligence algorithm, wherein: inputs to the artificial intelligence algorithm comprise the normalized environmental data; and outputs of the artificial intelligence algorithm comprise environmental risks, consequences, and probabilities associated with at least one environmental event 908 — Modifying at least one planned project using the environmental risks, consequences, and probabilities associated with the at least one environmental event End

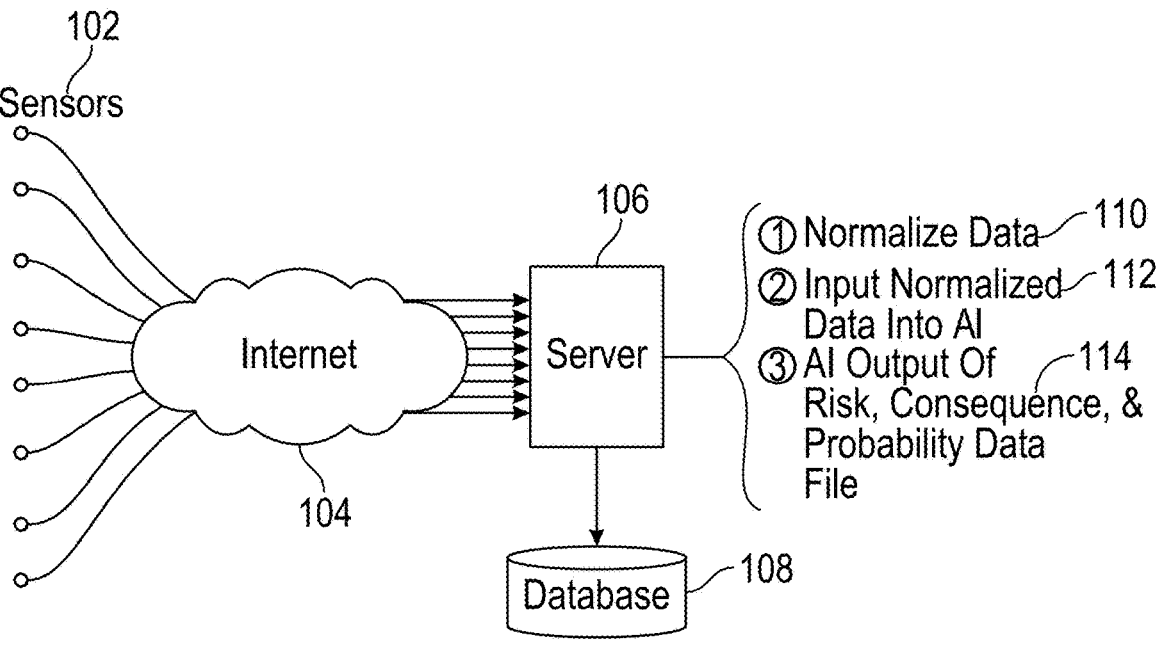

102

Sensors

Internet

104

106

Server

① Normalize Data — 110
② Input Normalized — 112
  Data Into AI
③ AI Output Of — 114
  Risk, Consequence, &
  Probability Data
  File Database — 108

FIG. 1

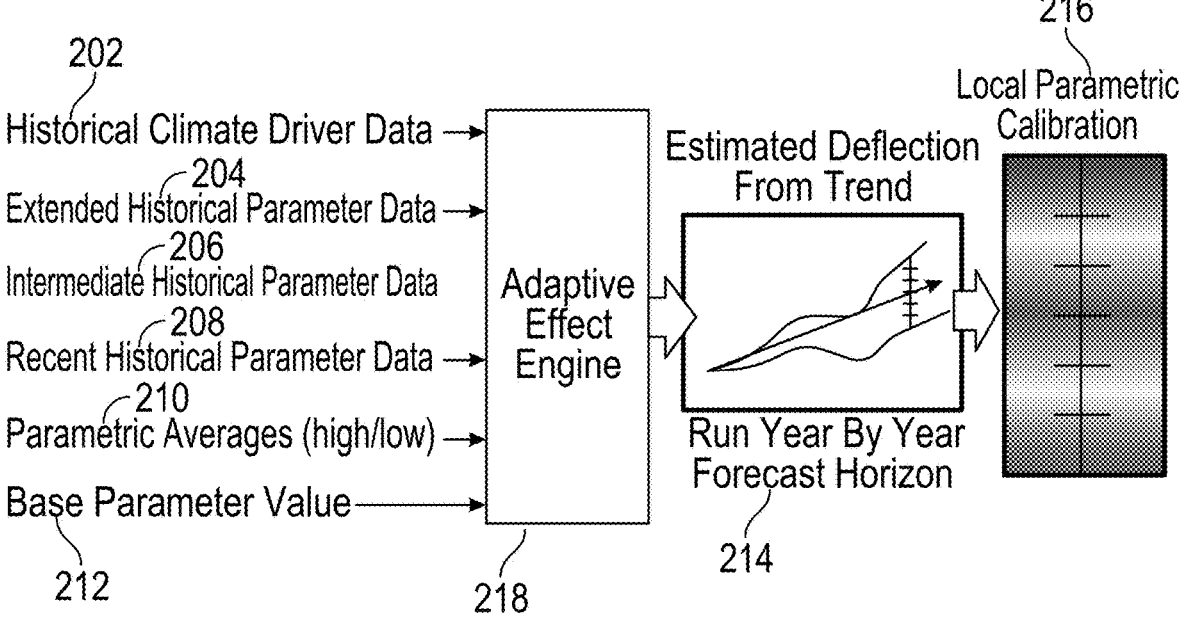

202

Historical Climate Driver Data →

204
Extended Historical Parameter Data →

206
Intermediate Historical Parameter Data →

208
Recent Historical Parameter Data →

210
Parametric Averages (high/low) →

Base Parameter Value →

212

Adaptive
Effect
Engine

218

Estimated Deflection
From Trend

Run Year By Year
Forecast Horizon

214

216
Local Parametric
Calibration

FIG. 2

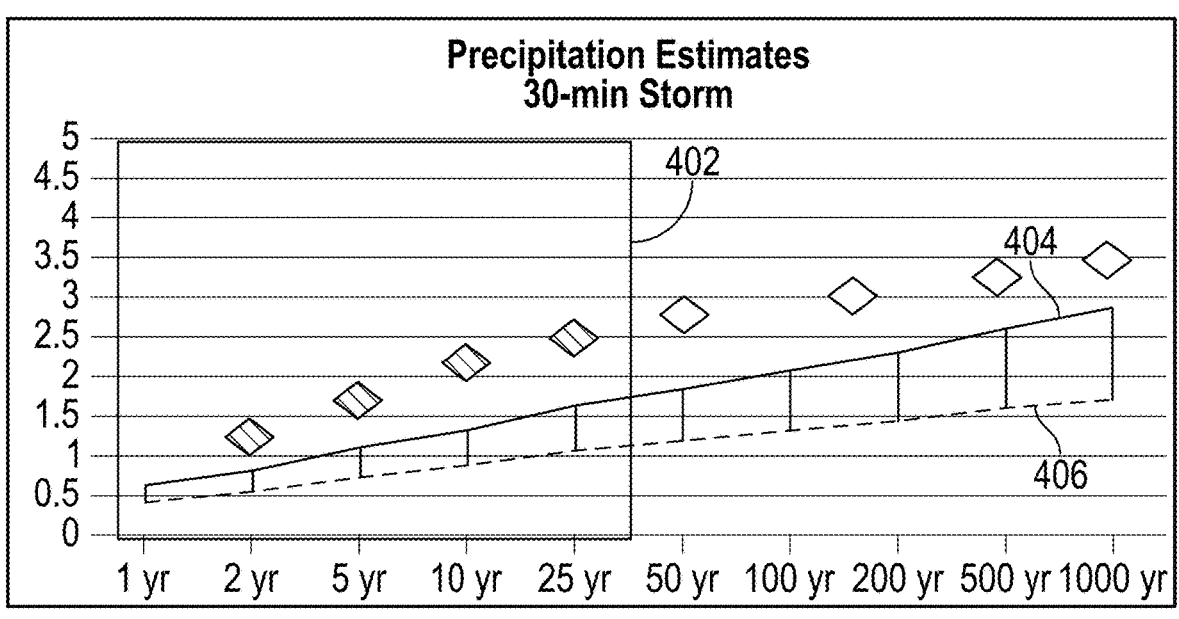

FIG. 4

Connecting Changing Impulses to Metrics that Matter

502

506

Climate Change Impulses

Water Level Change

Precipitation

Temperature

Agricultural Metrics

Salinity                    504

Encroachment

Moisture Content

Groundwater Level

Streamflow

Contaminant Concentrations

Degree-Day Accumulation

Cold-Hour Accumulation

Production & Cost Impacts
Yield

Condition

Location Migration

Infrastructure Alignment

Crop - Livestock ROI

Plant - Livestock Ratios

Disaster Production Denial

Management Overhead

Research Investment

Metrics that Matter ← Impulse → Object → Metrics that Matter

602    +   ↑ 610             602

Metrics that Matter ← Effects ← Response → Metrics that Matter

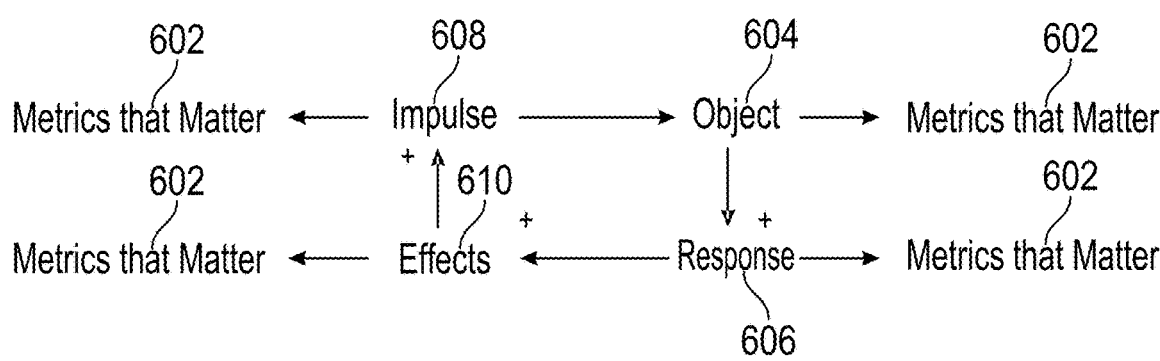

702        704        706

708

What is the precipitation design for 2040?
- analyze 1.5" daily events
- analyze 3.0" daily events
- analyze 4.5" daily events

710

Analyze historical context for time-intensity interactions

712

Comparison of Storm Intensity
2-, 5-, 10-, 25-, 50-, 100 year for 24-hour storms

☑1970
☑2022
☑2040

2 yr   10 yr   25 yr   50 yr   100 yr

714

Determine what scenario to design for:
- Identify Rainfall band of interest
- Data Driven selection algorithm
- Forecast Storm Series Variations
- Identify Identical Watersheds across variations

716

Modify infrastructure plans based on identified watersheds

FIG. 7

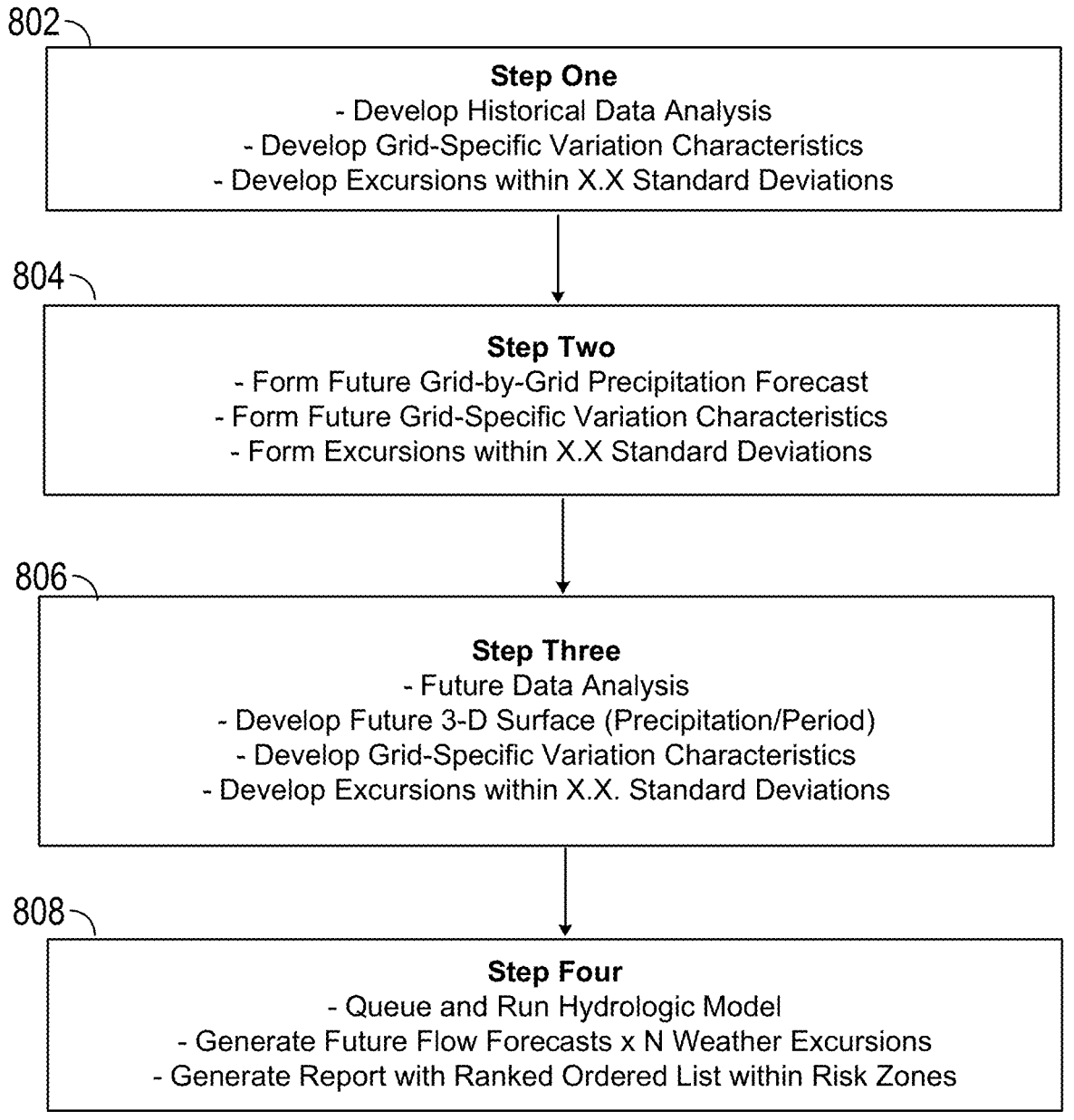

802 —
Step One
- Develop Historical Data Analysis
- Develop Grid-Specific Variation Characteristics
- Develop Excursions within X.X Standard Deviations 804 —
Step Two
- Form Future Grid-by-Grid Precipitation Forecast
- Form Future Grid-Specific Variation Characteristics
- Form Excursions within X.X Standard Deviations 806 —
Step Three
- Future Data Analysis
- Develop Future 3-D Surface (Precipitation/Period)
- Develop Grid-Specific Variation Characteristics
- Develop Excursions within X.X. Standard Deviations 808 —
Step Four
- Queue and Run Hydrologic Model
- Generate Future Flow Forecasts x N Weather Excursions
- Generate Report with Ranked Ordered List within Risk Zones

FIG. 8

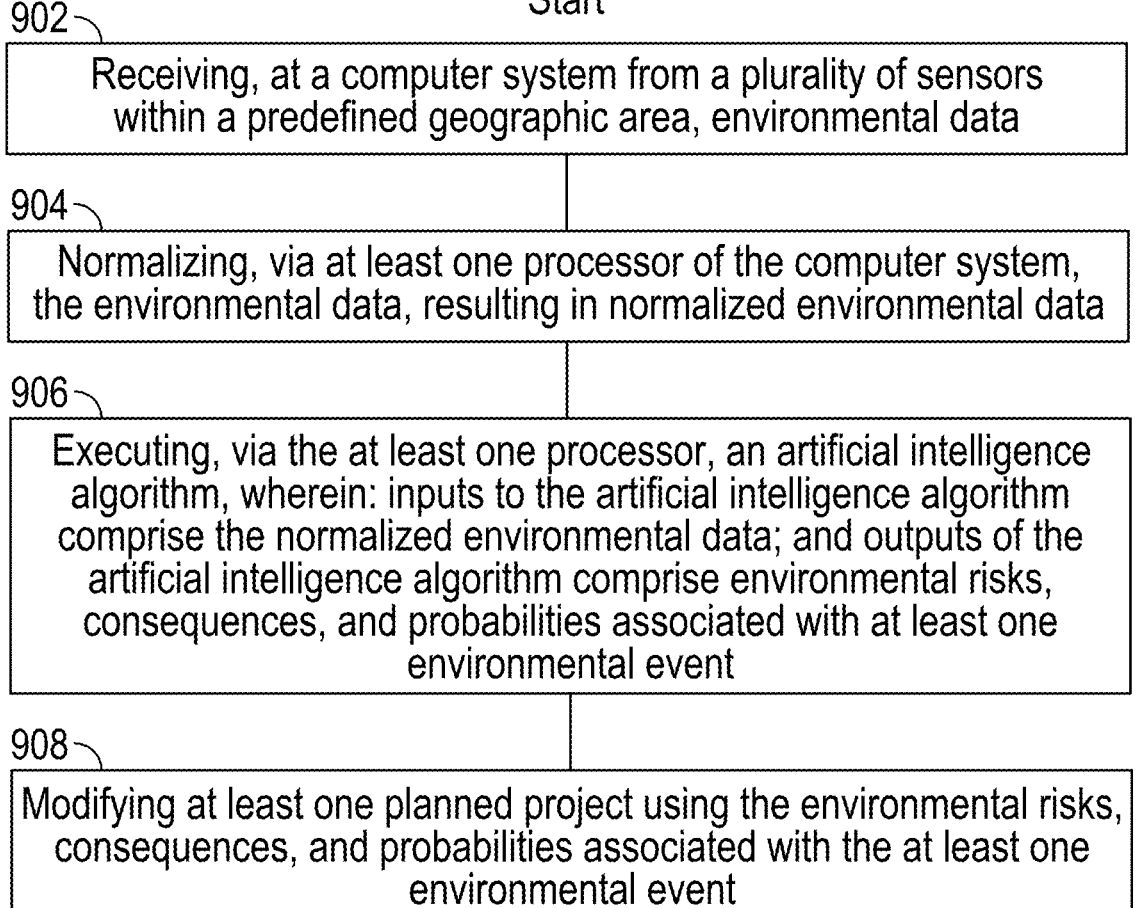

Start

902 ⌐
Receiving, at a computer system from a plurality of sensors within a predefined geographic area, environmental data 904 ⌐
Normalizing, via at least one processor of the computer system, the environmental data, resulting in normalized environmental data 906 ⌐
Executing, via the at least one processor, an artificial intelligence algorithm, wherein: inputs to the artificial intelligence algorithm comprise the normalized environmental data; and outputs of the artificial intelligence algorithm comprise environmental risks, consequences, and probabilities associated with at least one environmental event 908 ⌐
Modifying at least one planned project using the environmental risks, consequences, and probabilities associated with the at least one environmental event End

FIG. 9

SYSTEMS AND METHODS FOR FORECASTING OPERATIONAL AND STRATEGIC IMPACTS OF CLIMATE CHANGE ON WATER QUALITY AND/OR QUANTITY

PRIORITY

The present application claims priority to U.S. provisional patent application No. 63/300,756, filed Jan. 19, 2022; and U.S. provisional patent application No. 63/421,824 filed Nov. 2, 2022. The entire contents of each and every one of these applications are incorporated herein by reference in their entirety.

BACKGROUND

1. Technical Field

The present disclosure relates to making forecasts of the impact of climate change, and more specifically to the impact on water quality and/or quantity.

2. Introduction

The effect of abnormal/extreme events on water quality and/or water quantity is of immense importance to not only human health, environmental well-being, and animal/agricultural concerns, but also to communities in terms of future community planning, infrastructure design, industrial permitting, monitoring activities (sensor deployments, field testing, and citizen reporting), mitigation and response planning, and community resilience strategy development, project planning & sequencing, project funding & scheduling, and project implementation priority.

Life safety, health and well-being, environmental security, and socio-economic activity are inextricably linked to a quantitative understanding of probable events on water quality and/or quantity. However, much of the body of research, publication, and modeling associated with shifting climate patterns addresses large scale, global, and/or continental trends and effects. While these efforts are valuable in terms of establishing the framework for a collective solution, they do not provide discrete information suited for use at local levels in planning, designing, prioritizing, budgeting, and constructing climate change mitigation and protection projects.

SUMMARY

Additional features and advantages of the disclosure will be set forth in the description that follows, and in part will be understood from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Disclosed are systems, methods, and non-transitory computer-readable storage media which provide a technical solution to the technical problem described. A method for performing the concepts disclosed herein can include: receiving, at a computer system from a plurality of sensors within a predefined geographic area, environmental data; normalizing, via at least one processor of the computer system, the environmental data, resulting in normalized environmental data; executing, via the at least one processor, an artificial intelligence algorithm, wherein: inputs to the artificial intelligence algorithm comprise the normalized environmental data; and outputs of the artificial intelligence algorithm comprise environmental risks, consequences, and probabilities associated with at least one environmental event; and modifying at least one planned project using the environmental risks, consequences, and probabilities associated with the at least one environmental event.

A system configured to perform the concepts disclosed herein can include: at least one processor; and a non-transitory computer-readable storage medium having instructions stored which, when executed by the at least one processor, cause the processor to perform operations comprising: receiving, from a plurality of sensors within a predefined geographic area, environmental data; normalizing the environmental data, resulting in normalized environmental data; executing an artificial intelligence algorithm, wherein: inputs to the artificial intelligence algorithm comprise the normalized environmental data; and outputs of the artificial intelligence algorithm comprise environmental risks, consequences, and probabilities associated with at least one environmental event; and modifying at least one planned project using the environmental risks, consequences, and probabilities associated with the at least one environmental event.

A non-transitory computer-readable storage medium configured as disclosed herein can have instructions stored which, when executed by a computing device, cause the computing device to perform operations which include: receiving, from a plurality of sensors within a predefined geographic area, environmental data; normalizing the environmental data, resulting in normalized environmental data; executing an artificial intelligence algorithm, wherein: inputs to the artificial intelligence algorithm comprise the normalized environmental data; and outputs of the artificial intelligence algorithm comprise environmental risks, consequences, and probabilities associated with at least one environmental event; and modifying at least one planned project using the environmental risks, consequences, and probabilities associated with the at least one environmental event.

BRIEF DESCRIPTION OF THE DRAWINGS

FIG. 1 illustrates an example system embodiment;

FIG. 2 illustrates an example process for categorizing impacts;

FIG. 4 illustrates an example of using feedback and additional training data to iteratively train the neural network;

FIG. 5 illustrates an example of mapping impulses to metrics that matter to consequences;

FIG. 6 illustrates an example of converting impulses into metrics that matter;

FIG. 7 illustrates an example of modifying plans based on data projections;

FIG. 8 illustrates an example of a multi-attribute decision making processes to determine risk, consequence, and probability of hydrological events;

FIG. 9 illustrates an example method embodiment; and

DETAILED DESCRIPTION

Figure 3:
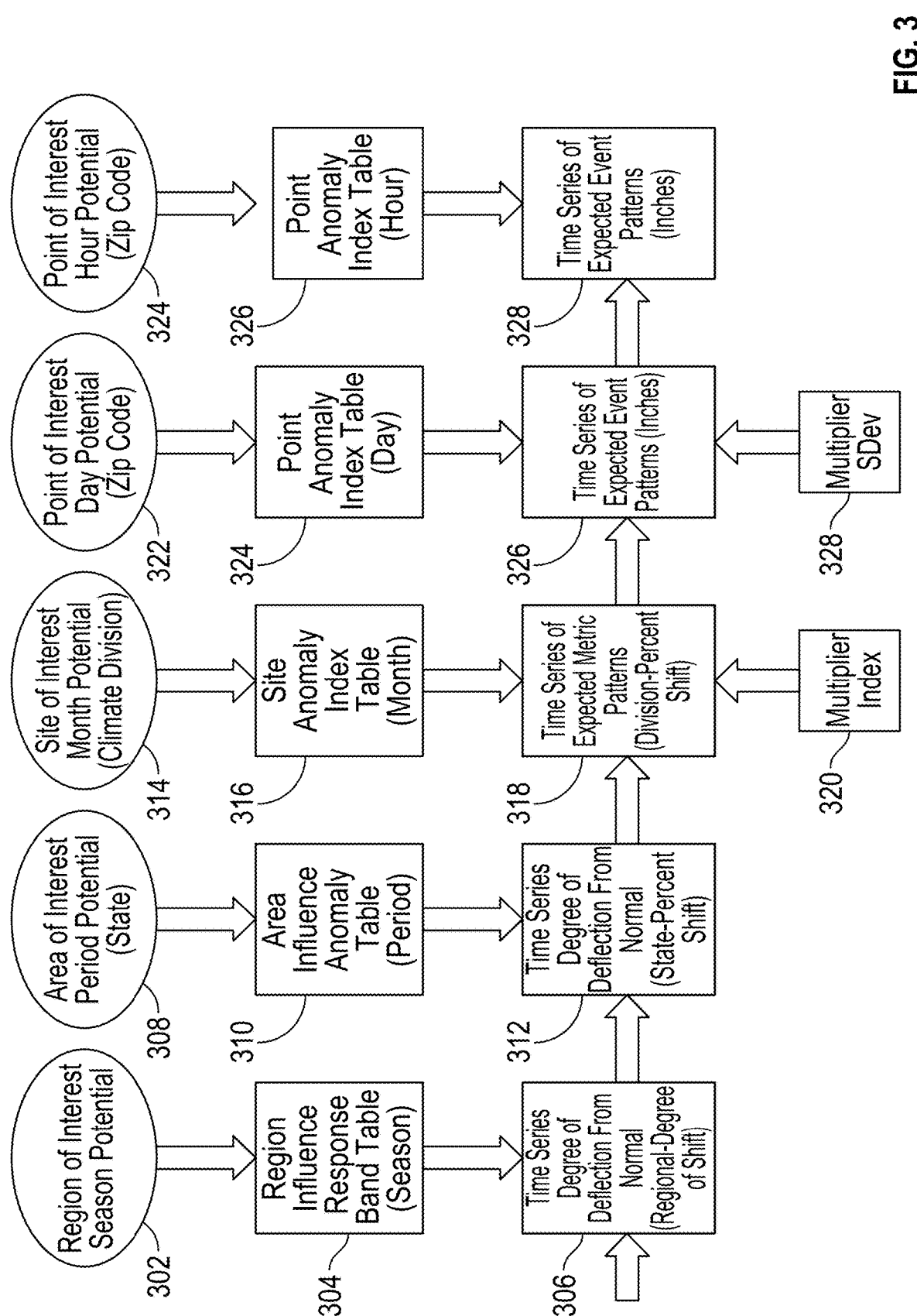
FIG. 3 illustrates an example of using web-scraped contaminant data to form a neural network.

Various embodiments of the disclosure are described in detail below. While specific implementations are described, it should be understood that this is done for illustration purposes only. Other components and configurations may be used without parting from the spirit and scope of the disclosure.

Knowing the probable impact of an event on water quality related metrics (e.g., contaminants, concentration, and physical properties) is important to understanding how changes in source water quality affect municipal water systems, industrial activities, and agricultural production cycles. Knowing the probable impact of an event on water quantity related metrics (e.g., volume, velocity, and flood stage) is equally important in understanding how increased runoff can affect preparation, response, and recovery activities.

To determine the future climate-determined-environmental-conditions related to water quantity and quality, one first needs to identify what the conditions are expected to be. This identification is done by taking inventory of metrics related to climatic and environmental indicators related to water quantity and quality. In order to be useful, the climatic and environmental metric inventory must be related to a specific geographic level such as (but not limited to) those defined by NOAA (National Oceanic and Atmospheric Agency): climate regions (largest area), the states (intermediate area), climate divisions (lesser intermediate area), and the 5 km×5 km grid system (smallest area). Other geographic levels are likewise within the scope of this disclosure. Those climatic and environmental conditions associated with water quality and/or quantity can include, but are not limited to: historical, current, and projected future land cover data, socio-economic activity data, soil data, water level data (e.g., surface water and ground water), atmospheric data, and meteorological data (such as, temperature, humidity, precipitation, and wind). Such data, real-time and historical, is generated by a constellation of sensor systems and data systems maintained by public entities (NOAA, the National Weather Service (NWS), and others) and private parties (e.g., The Weather Channel, the Microsoft Planetary Computer, and others) while forwarding looking data is generated using an artificial intelligence (AI) managed future-data series generation system to develop localized, time-discrete future scenarios. This data is useful in and of itself. However, it becomes more valuable when it is mapped to risks and consequences of interest. For example, one may want to plan for the resilience of a particular public or private structure regarding inundation by flash flooding. In this case, the type of data useful to make such a determination can include data related to rainfall event intensity (inches/hour), rainfall event duration (hours), and/or rainfall event total (inches). Of interest also, would be data that indicates how that rainfall is distributed over the upstream watershed area, what surface water quality influencing contaminant loading would be expected, what levels of flow (cubic feet/sec) would be expected over a period of time, what flow velocity profile would be expected, and what the elevation of the flow surface would be expected relative defined to local flood stages. Such data, made available to a party, will be valuable in workstreams that seek to determine risk, consequence, and probability questions that dominate resilience planning, design, budgeting, and constructing mitigation and protection projects.

Systems configured as disclosed herein allow for understanding the full range of effects of shifting climate patterns on water quantity and quality for a given location. Specifically, the methods described herein address quantifying the impact of both short-term weather events and extended weather patterns for a given location. In the short-term case, exemplary weather events can include precipitation (e.g., rain and/or snow), temperature variation (e.g., a temporary heat wave and/or a temporary deep freeze), humidity variations (e.g., extreme high humidity and/or extreme low humidity), and/or wind pattern variations (e.g., high wind and/or stagnation). Systems configured as disclosed herein receive that weather data and provide insight into the relatively immediate effects on water quantity and quality of an independent occurrence and/or collective concurrence. In the extended case, weather patterns can include drought, increased frequency of high intensity rains, increased temperatures, changing prevailing humidity, and/or shifting prevailing wind patterns. Systems configured as disclosed herein can likewise take this data and provide insight into longer-term effects on water availability, source water distribution, and water level changes in both surface and ground water, and water quality associated with the extended periods of independent and/or multiple interacting extended weather patterns. These insights can take the form of projections regarding those future conditions which can be used by the system to update or modify planned infrastructure projects or other planned events.

As stated above a significant problem is that much of the body of research, publication, and modeling associated with shifting climate patterns addresses large scale, global, and/or continental trends and effects. While these efforts are valuable in terms of establishing the framework for collective solution, they do not provide discrete information suited for use at local levels in resilience planning, designing, prioritizing, budgeting, and constructing mitigation and protection projects. For example, many forecasts on climate change provide information related to changing temperature and precipitation patterns at a global level, a regional level, or a wide-area level. Further, the time periods reflected in these forecasts is generally given at the expected annual or monthly levels. While that information can be useful, it is generally not applicable at the local level (e.g., a watershed level), nor is it available at the multi-day storm series level, the daily, nor hourly precipitation levels that are required to support realistic impact and risk assessment. What is needed at the local level is a forecast over a time horizon meaningful to the range of stakeholders (i.e., residents, businesses, municipal governments, state governments, and regional socio-economic-environmental alliances). What the stakeholders need to know is: how will change affect our local crop production, stormwater runoff, ability to support water intensive industry, drinking water supply, ability to properly treat and discharge wastewater, and the ability of infrastructure to operate under climate stress events. These questions pose a new demand on all involved in resilience planning, design, budgeting, and constructing mitigation and protection projects.

The invention described herein addresses this problem across a range of use cases associated with key water quantity and quality dependent sectors of the socio-economic-environmental system: agriculture, stormwater, industry, drinking water, wastewater, and infrastructure. For example:

in terms of agriculture, a primary question may be 'will one expect enough rainfall or too much rainfall to support crop development during the growing season?' 'Will the water quality be suitable to support food and feed safety requirements and will it support the necessary biological processes to fully develop the crops within the allowable season?';

in terms of stormwater, a primary question may be 'will one expect a significant capacity shortfall in terms of stormwater management infrastructure given the changing rainfall intensity patterns?' Will the water quality be such that it negatively affects the surface water system and its users & stakeholders in terms of ability to support riparian ecosystems, food production, industrial production, drinking water sources, safe wastewater discharges, commercial and sport fishing, and water recreation?';

in industry, a primary concern may be 'will one expect a sufficient availability of suitable surface water to support production requirements?' Will the water quality be suitable to support product, equipment, and process safety requirements to support economic production during periods of climate induce short-or long-term stress?';

in drinking water, a primary concern may be 'will one expect that new contaminants and/or current contaminants at higher concentrations than expected be ingested at surface water intakes requiring additional investment in source water protection means and methods?' Will the water quality be suitable to support drinking water safety requirements given current and/ or future treatment processes and/or are their sufficient suitable groundwater sources available to operate at current and a future expected drinking water demand levels?';

in wastewater, a primary concern may be 'will wastewater treatment processes be sufficient to support neutralization at increased volume and/or contaminant constituency to allow return of effluent to surface water bodies?' Will the water quality be suitable to support the maintenance of safe surface water quality levels given expected future wastewater treatment discharge loads?'; and in infrastructure management, a primary concern may be 'will one expect specific elements of both public and private infrastructure operating at a minimum viable capacity and/or efficiency to support socio-economic-environmental needs while under both short-and long-term climatic stress?'

For example, consider the case of a wildfire caused by extended drought and heat, and fueled by short-term high winds, low humidity, and insufficient precipitation. In such an event, large amounts of ash may find its way into a river increasing pH. When this higher pH water arrives for induction into a municipal drinking water system, there can be catastrophic consequences if high pH drinking is released directly into the distribution system for consumption, and there can be unintended consequences if mitigation measures are taken to deal with the large amounts of ash to bringing pH back into ranges safe for human consumption, distribution system integrity, and/or industrial intake. For both scenarios, the municipal drinking water system authorities need to be aware of the underlying problems.

Systems configured as described herein can identify how long-term and short-term weather and environmental conditions can positively or negatively impact both water quality and/or quantity. Examples of positive or constructive points of inquiry which the system can return include: future water availability, surface water distribution, and water quality, such that the system can be queried for future water availability, surface water distribution, and water quality for a given area, and the system can provide those predictions. Examples of negative or destructive points of inquiry for which a system user can search can include: future runoff induced flash flood potential, the impact of drought on water availability/distribution (effecting both quantity and quality), the impact of forest fires on runoff (effecting both quantity and quality), the impact of major storms (e.g., thunderstorms, tornadoes, and hurricanes) on runoff (effecting both quantity and quality), and the impact of significant numbers of earth disturbances such as earthquakes or soil saturation induced landslides (effecting both quantity and quality). To do this, the system uses a combination of sensors distributed throughout the globe, continent, nation, region, state, locality and/or other geographic region being analyzed, with these sensors capable of identifying specific changes within the major atmospheric influences (such as El Niño, the Madden-Julian Oscillation, and the Pacific/North American teleconnection pattern), changes within the continental influences (such as the Polar Vortex, and the Jet Stream), changes within the regional influences (such as the Pacific Northwest Atmospheric River), changes within regional influences (such as the Gulf Stream), and changes within highly localized influences (such as topographically generated micro-climates). For example, to detect changes to the polar vortex/jet stream, the sensors may include temperature and/or wind speed temperatures which, combined with the sensor locations, can provide data about how the polar vortex and/or jet stream are changing. Likewise, detection of El Niño/La Niña (El Niño begin above-average sea-surface temperatures across the east-central equatorial Pacific, and La Niña begin below-average sea-surface temperatures across the east-central equatorial Pacific) can rely on satellite temperature measurements, radar altimeters, buoys, or other sensor mechanisms.

The sensor data, representing measurements throughout the geographic area being analyzed, can be associated with the weather events and/or trends relevant in a particular location, and can be further modified to include to what degree future data will be different from current data. These insights are developed by a process that is supported by a custom algorithmic bundle that specifically scans the telltale data streams to reveal technical signals of short-, medium-, and long-term trends at the necessary levels (discussed above) required to support specific climate-related public and private action and investment decisions.

The system uses the developed epoch-series data to support follow-on use case-aligned workflows (i.e., planning, design, prioritization, budgeting, and implementing resiliency enhancing projects), to: (1) identify climate induced impulses (actionable changes to the quality of life or infrastructure in an area) related to water quantity and quality; and/or (2) develop estimates of future risk in terms of event location, intensity, and/or duration across a range of probabilities.

To support these workflows, normalization can be accomplished via computational routines. Stratification of risk estimates can be defined within a particular socio-economic-environmental sector of interest. Similarly, likelihood of occurrence expressed in terms of probability can be stratified such that consequence estimates can be generated. The three values—risk, consequence, and probability—which are generated by the system—become actionable when considered in multi-attribute decision making processes. If, for example, the system detected a potential for an impulse to grow over time due to climate change via a specific process.

The first step in the process involves examination of historical climatology data on an hourly level. Sources for such data can include both public and private data, such that a 3-D climatic experience surface can be generated to reflect differences between one micro-climate zone and its neighboring zones. The 3-D climatic experience surface can be expanded from the location of interest upstream to include the areas that constitute the full expected collection of watersheds that influence the surface water at the location of interest.

The second step is to build a mirror image of that 3-D climate experience surface that reflects the future time-period of interest. The 'future view' can be developed using a custom time-series forecasting tool that considers the 'current view' set (please note: the set concept can incorporate the range of variation potential such that the set is comprised of a number of unique surfaces) as the base point. The trajectories to drive to the 'future view' set can be developed using AI to generate change scenarios aligned with the periodically updated International Panel on Climate Change (IPCC) Representative Concentration Pathways (RCPs) (e.g., for $CO_2$) that characterize the internationally accepted range of future macroscopic environments in conjunction with the data available via the NOAA Climate Resiliency Toolkit. The 'current view' to 'future view' can transform vectors that describe the range of change within the observed values, change occurrence periodicity, change polarity, change momentum, and/or change epoch longevity. Together, these technical indicators can be recorded as vector sets that describe the finite climatic response characteristics of a historically-observed microclimate. For each of these vectors, AI guided epoch series can be used to support development and exploration of continuous short, intermediate, and long-term scenario ranges.

The third step is to translate annual and monthly data derived from the NOAA climate resiliency toolkit into daily and hourly precipitation potential. To do this the system can use a multi-threading search and detection algorithm to build a view of future daily and hourly precipitation.

The fourth step is to identify storm patterns of interest and rank order them in terms of impact. To do this, the system can run multiple (e.g., hundreds, thousands, millions, etc.) iterations of a hydrological model over one or more time frames (such as, but not limited to, the year, the seasons, overlapping three month sequences, select months of interest, and/or a specific month of interest). The system can be trained to find outliers, such as (but not limited to), the 'least harm', the 'most likely harm', and/or the 'most harm' scenarios in which the 'harm' utility function is defined as volume of surface runoff. The system can then publish recommended bounding storm series for use in planning.

Standing alone, the individual event values (present and future) for two potential events (A & B), can represent a comparative risk assessment, however the individual event values fail to address the consequences if those risks are fully realized. The system can place a value on the risk in terms of cost, number of homes or businesses affected, number of lives lost, number of lives impaired by injury for Event A and Event B, etc. With risk metrics and quantification defined as described above, the end product of the process can be a comparison of risk change over time given an event definition as described above. With the data fully developed, the user can select an event in terms of total precipitation, days of precipitation, hourly intensity of precipitation, etc., such that the effects of the individual event values can be generated at any future time-slice expressed by selection of the year-of-interest. For example, the user can select a location and multiple events, and the system can generate a comparative risk assessment for the different events and generate individual event effects for each event. Graphic illustrations generated by the system can include a depiction of the multi-day flow levels on an hour-by-hour basis in the form of a conventional hydrograph, where the conventional hydrograph can include one or more annotations regarding: peak flow (i.e., in cubic feet per second); a total volumetric flow from the beginning to the end of the elevated flow period; and/or a number of hours that the resulting flow is expected to exceed a user defined maximum channel capacity, a stream/river bed capacity, and/or a volume above which channel path and cross-sectional shape integrity is threatened.

To close the decision matrix development cycle, the system generates estimates of probability in terms based on recurrence intervals for events A and B. Note that, in advanced cases where event-to-event interaction can generate an amplified risk and consequence, the system can examine three scenarios: unrelated serial occurrence, unrelated concurrent occurrence, and/or related dependent occurrence.

Based on a continuous analysis of a potential risk, consequence, and probability of future negative impacts on one or more elements of the on socio-economic-environmental elements particular to a specific location, the system can filter out which event, trend, and effects data are to be reported to an end user who seeks to understand the climatic-environmental water-related effects for which they have concern. For example, if a probability of threat to infrastructure is detected so far below the threshold of concern that it poses no risk or consequence, the system can filter reporting of that threat. Other threats, which have a sufficient probability to pose a risk and consequence of concern, can be reported to the end user along with supporting data that addresses the climatic-environmental impulse metrics, the location of concern, the probability of occurrence, the level of risk presented, and the elements of socio-economic-environmental activity that could suffer consequence.

In some configurations, the system can use Artificial Intelligence (AI) to combine identify one or more short-term events and/or long-term trends. For example, the system can train a neural network to recognize combination events and/or trends from a range of possibilities related to precipitation, temperature, humidity, and/or wind. Once trained, the inputs to the neural network could be, for example, the sensor data, such as detection of individual meteorological metrics. The neural network can then output detected event and/or trend markers detected in specific geographic areas, such that the projected events/trends are provided by the AI/neural network to the system. Training of the AI/neural network can occur via any method known to those of skill in the art. As outputs are received from the AI/neural network system, experts can review the data and provide feedback regarding its accuracy. That feedback can be added to a corpus of training data, such that future iterations of the neural network are improved. This feedback process and iterative retraining of the neural network is referred to as "supervised learning."

In addition, the corpus of training data used to build the AI can increase over time using additional data acquired through web-scraping. As the system continues web-scraping, new data, or updated data, is added to the body of data. Periodically, or when the system reaches a threshold increase in data, the system can retrain the neural network using the updated training data. In some configurations, the neural network can prune or remove old data or intermediate nodes which are no longer useful in providing accurate outputs. Because constantly adding to the training data can result in ever-increasing training times for the AI, the ability to remove or prune data which is not useful to accurate outputs can result in saved computational time and/or power. For example, if shifting weather patterns led to an increase in the frequency of intense rainfall events along with changes in landcover and land use, one would see a change in both the stormwater runoff volume (quantity) and the stormwater runoff contaminant constituency (quality). These changes would be reflected in the data made available to the A.I. such that the system would 'learn' the new pattern as the A.I. continuously compares input data to output data through the course of its normal operational cycle. As significantly different patterns emerge, old patterns are relinquished to an archive for reference in use cases involving the determination of rates of change in one or more of the metrics of interest in such matters.

Systems configured as disclosed herein can use the outputs of the AI/neural network (i.e., projections of current and/or future water conditions, identification of current and/or future water-related events, etc.) to identify how people and/or infrastructure which are, or will be, effected by the AI outputs. For example, consider a city which has a river running through it, and several bridges crossing the river. The city in this example is planning to renovate one of the bridges, and various aspects of the planned renovation are uploaded to the system (such as bridge length, height above the river, etc.). The system also receives hydrological data for the geographic area around the bridge in question, historical flooding data, and a history of precipitation events (preferably as much precipitation data as is available, through a portion of such data (e.g., the past twenty years) can also be used). The system analyzes the historical flooding data and the history of precipitation events, identifying correlations between precipitation and flooding events. Preferably, the identified correlations identify the historical contexts based on time-intensity interactions, such as the amount of water that fell to create the 6-hour rainfall record, the 12-hour rainfall record, the 24-hour rainfall record, the wettest month on record, etc. Using these historical contexts, the system can compare the storm intensities and determine a water distribution projection which is a mixed value representing when 100% of rainfall is collected in a given time period (e.g., 3 hours), when 60% of the rainfall is collected in the same time period, and when 20% of the rainfall is collected, such that the water distribution projection is made up of multiple individual projections. In some configurations, additional or fewer rainfall projections can be included in the combined water distribution projection. This combined water distribution projection uses the recorded information from previous storms, and projects how future storms will likely affect the city with respect to water levels, water quality, etc.

Once the combined water distribution projection is generated, the system can apply that information to the hydrological data and the proposed bridge renovation data. Based on how the water distribution projection is applied to the hydrological data, the system can determine if the proposed renovation will be adequate for the projected water levels, water quality, etc. In this example, the system can compare the proposed bridge height of the renovated bridge against the projections for what a 100 year storm will look like in the future and, if necessary (i.e., the proposed bridge would not be high enough over the river to survive the flood), modify the proposed bridge height's minimum requirement based on the projected hydrograph.

FIG. 1 illustrates an example system embodiment. As illustrated, multiple sensors 102 collect data regarding metrics of interest as related to climate data and make them available across the internet 104 by delivering the metrics to a server 106. In practice, the illustrated server 106 may be more than one server, or may be a cloud-based computing platform (such as AZURE or AMAZON WEB SERVICES).

The server 106 receives the sensor 102 data, and receives a list of categorized climate metrics of interest from a database 108. The server 106, using at least one processor, normalizes the sensor data 110, then inputs the normalized data into an AI algorithm 112, which can identify the relationship between various metrics, the various values associated with each metric, and the water quantity and quality metrics that map to resiliency outcomes associated with agriculture, stormwater, industry, drinking water, and/or wastewater sectors. The system can then filter out which of the sectors may be negatively affected by weather events and/or prolonged trends. Further the A.I. will generate an export file for data of interest 114 (e.g., risk, consequence, and probability of future water quantity/quality) to be consumed by end-users in follow-on workflows (i.e., planning, design, prioritization, budgeting, and implementing resiliency enhancing projects).

FIG. 2 illustrates an example process for determining the effect of shifting climate on a metric of an effect of interest. In this generalized case, various metrics 202, 204, 206, 208, 210, 212 are pulled from the normalized database to provide input to the Adaptive Effect Engine 218. The engine 218, using A.I., can generate time series forecasts 214 over time horizons of (for example) 2-, 5-, 10-, or 25-years. The timeseries presents a central path which is bounded on the optimistic and pessimistic sides by bands that reflect a defined level of uncertainty. At any point along the time series, the departure from baseline can be assessed in terms of degree of departure. This departure from baseline can, for any point in time, be displayed/described as a local parametric calibration 216, illustrating how much deviation from the baseline exists within the metrics 202, 204, 206, 208, 210, 212. The process is the same for precipitation, temperature, humidity, and wind. The product of this element of the system is the degree of change in the impulse(s) that drive risk and consequence at a given level of uncertainty.

FIG. 3 illustrates an example of method localization. The determination of the expected degree of departure of projected water quantity/quality from baseline values sets the basis for localization. Localization is accomplished by blending location specific data (progressing from large areas down to specific locations) with the degree of departure time series. Localization can be accomplished across a range of levels from a number of defined climate regions down to the zip code. Along with localization, the system supports progressively more finite temporal analysis. As illustrated, the system has a region of interest 302 associated with season potentials, an area of interest 308 (i.e., a sub-portion of the region of interest 302, such as a state or province) with a period potential, a site of interest 314 with a month potential, a point of interest 322 with a day potential, and a point of interest 324 with an hour potential. As the localization progresses from region 302 to zip code 322, 324, the time period of the forecast can progress from season to month to day to hour, or any other temporal metric.

The data associated with the different regions 302, areas 308, sites 314, and points of interest 322, 324 is organized into tables 304, 310, 316, 324, 326 associated with the different geographic areas. Using that organized data 304, 310, 316, 324, 326 generates time-series deflection-from-normal data 306, 312, 318, 326, 328 for each table 304, 310, 316, 324, 326. As illustrated, the data becomes progressively more finite as it progresses from regional time-series data 306 to time series associated with point anomalies 326, 328.

Beyond the supporting of the user on a progressively more finite locations and time slices, the system can provide a user interface to explore the range of possibility. Multiplier controls 320, 328 allow the user to ask questions such as 'would if the actual future values are higher or lower than initially displayed?' In addition, the user can inquire as to the effect of greater degrees of variation in a metric than has been seen in the past. Together these controls allow the user to assess the degree of sensitivity that is associated with risk, consequence, and probability.

FIG. 4 illustrates an example of displaying a shift in precipitation intensity risk and probability. In the example displayed, the historical storm intensity values are illustrated within the envelope of historic observation that are assigned to a specific recurrence interval ranging from 2 to 1000 years. Because specific recurrence intervals are specified in design practices, changes in the level of intensity of a storm (inches/hour) associated with a recurrence interval are important in terms of resiliency planning. It becomes a decision whether to design against the past (the upper bound of the historic envelope 402) and the future possibility generated by the system (displayed as diamonds outside the envelope 402 in this illustration). An example problem would be that one wishes to design a culvert for a secondary road drainage system. The design standard may call for a 25 year storm as the standard but in fact there is potential that in 10 years the 25 year storm may be significantly higher. As such the system provides indication of risk (intensity) 404 and probability (recurrence interval) 406 that allows decision makers to assess the consequence given future year storms.

FIG. 5 illustrates an example mapping impulses 502 to metrics that matter 504 to consequences 506. Mapping a climate change impulse 502 to the metrics that matter 504 and then to consequences 506 that can be assigned present and future cost values is a context sensitive activity that is required in understanding the priority of a proposed mitigation or protection option. To meet this need, the system embodies mapping templates that are associated with agriculture such as (but not limited to): stormwater, industry, drinking water, wastewater, and infrastructure. The mappings support computational flows that carry the information developed in the determination of degree of deflection, finite parametric resolution associated with localization and time slice reduction, and risk and probability assignment to a consequence calculator. In this step of the method, users can enter cost estimates and select growth factors to translate Preset Value estimates into Future Value estimates for a given event intensity. This business case element of the method serves as a cornerstone for selection and prioritization of mitigation and/or protection options.

FIG. 6 illustrates an example of converting impulses into metrics that matter. As illustrated in FIG. 5, the impulses 608 can be items such as water level change, an amount of precipitation, and/or change in temperature. The system can, using those impulses 608, generate metrics that matter 602. In addition, the system can use the impulses 608 to generate an object 604, such as a graph or chart, illustrating (for example) the impulse 608 over a period of time. The system, using that object 604, can generate metrics that matter 602 based on that object 604. The system can also generate a response 606 to a query based on the object, and generate yet another metric that matters 602 as part of that response 606. Finally, the system can also identify effects 610, such as production and cost impacts, which will come about based on the impulse 608, object 604, and subsequent response 606. The effects 610 can be used to detect additional impulses 608 and/or to generate additional metrics that matter 602.

FIG. 7 illustrates an example of modifying plans based on data projections. In this example, the system receives city infrastructure data 702, such as a map of roads and buildings within a geographic area. The system also receives hydrological data 704, including information about the reach of various floods within the city. For example, the hydrological data 704 may include data regarding the amount of flooding associated with the rivers and waterways within the city for different amounts of rainfall at different times of the year, during different seasons, different rain amounts, etc. The system can, using the hydrological data 704 and the infrastructure data 704, identify portions of the city 706 which become inaccessible due to different levels of flooding.

The system can, review the hydrological data 704 and the portions of the city 706 which become inaccessible and compare that data against different levels of precipitation 708. As illustrated, such levels can include 1.5" of rain, 3" or rain, or 4.5" of rain, though other configurations can have additional levels of rain, fewer levels, and/or more levels of rain. The system can analyze the historical context for time-intensity interactions 710, which reveals when certain storms had major effects (e.g., destruction, loss of power, etc.) upon the city. The results of the analysis 710 can include a comparison of storm intensities 712, which can identify the relative intensity of storms within "buckets" such as a 5 year storm, a 10 year storm, a 100 year storm, etc. Based on this information, the system can determine 714 for which scenario(s) to make modifications to the city infrastructure 702. For example, the system can identify the rainfall band of interest, use data selection algorithm(s), forecast storm series variations, and/or identify watersheds, to determine what aspects of the infrastructure 702 should be modified. The system can then make modifications to one or more infrastructure plans based on the identified watersheds 716 and/or any other data within the scenario review system.

FIG. 8 illustrates an example of a multi-attribute decision making processes to determine risk, consequence, and probability of hydrological events. As illustrated, in this example is a four step process 802, 804, 806, 808.

The first step 802 of the process involves developing a historical data analysis, such as (for example) an examination of historical climatology data on an hourly level. This historical climatology data can result in the development of grid-specific variation characteristics for a specific geographic area. Sources for such data can include both public and private data, such that a 3-D climatic experience surface can be generated to reflect differences between one microclimate zone and its neighboring zones. The 3-D climatic experience surface can be expanded from the location of interest upstream to include the areas that constitute the full expected collection of watersheds that influence the surface water at the location of interest. The system can also develop/generate excursions within a certain number (e.g., 1, 2, 3, or any other number (i.e., "1.5" or "X.X") of standard deviations from the mean of the historical data.

The second step 804 illustrated is to build a mirror image of that 3-D climate experience surface that reflects the future time-period of interest. This mirror image is a future grid-by-grid precipitation forecast, where the 'future view' can be developed using time-series forecasting that considers the 'current view' set as the base point. The system also forms future grid-specific variation characteristics, which identifies specific variations or outliers within the grid-by-grid precipitation forecast. The trajectories to drive to the 'future view' set can be developed using AI to generate change scenarios aligned with the periodically updated International Panel on Climate Change (IPCC) Representative Concentration Pathways (RCPs) (e.g., for $CO_2$) that characterize the internationally accepted range of future macroscopic environments in conjunction with the data available via the NOAA Climate Resiliency Toolkit. The 'current view' to 'future view' can transform vectors that describe the range of change within the observed values, change occurrence periodicity, change polarity, change momentum, and/or change epoch longevity. Together, these technical indicators can be recorded as vector sets that describe the finite climatic response characteristics of a historically-observed microclimate. For each of these vectors, an AI guided epoch series can be used to support development and exploration of continuous short, intermediate, and long-term scenario ranges. The system can also develop/generate excursions within a certain number (e.g., 1, 2, 3, or any other number (i.e., "X.X") of standard deviations from the mean of the historical data, and can use those excursions in identifying the grid-by-grid variation characteristics.

The third step 806 is a future data analysis. In this step 804, the system translates annual and monthly data derived from the NOAA (e.g., from the climate resiliency toolkit) into daily and hourly precipitation potential, resulting in a future 3D surface with predicted precipitation for each different period. To do this the system can use a multi-threading search and detection algorithm to build a view of future daily and hourly precipitation. The resulting 3D surface with predicted precipitation can also identify grid-specific variation characteristics and outliers. These outliers can, for example, be identified by developing/generating excursions within a certain number (e.g., 1, 2, 3, or any other number (i.e., "X.X") of standard deviations from the mean of the historical data, and can use those excursions in identifying the grid-by-grid variation characteristics of the future 3D surface.

The fourth step 808 is to identify storm patterns of interest and rank order them in terms of impact. To do this, the system can queue and run multiple iterations of a hydrological model over the year, the seasons, overlapping three month sequences, select months of interest, and/or a specific month of interest. The number of times the iterations can be executed can vary depending on the data available and/or the accuracy desired by a system user. The number of iterations can be, for example, e.g., hundreds, thousands, millions, etc. In some configurations, execution of the model can utilize a Monte Carlo or other data simulation system which relies on random variables or combinations of variables. The result from executing multiple iterations of the hydrological model is generation of future flow forecasts and a number N of weather excursions, which combined together can be used to find outliers, such as (but not limited to), the 'least harm', the 'most likely harm', and/or the 'most harm' scenarios in which the 'harm' utility function is defined as volume of surface runoff. The system can then generate a report with a ranked ordered list of risky locations, events, or other potential problems within the risk zones of the geographic area. This ranked ordered list can also be based on projected costs, harm (e.g., projected displacement or deaths), etc. This ranked ordered list can be used in planning, or can be used by the system in updating planned projects.

FIG. 9 illustrates an example method embodiment. As illustrated, systems configured as disclosed herein can receive, at a computer system from a plurality of sensors within a predefined geographic area, environmental data (902); and normalize, via at least one processor of the computer system, the environmental data, resulting in normalized environmental data (904). The system can execute, via the at least one processor, an artificial intelligence algorithm, wherein: inputs to the artificial intelligence algorithm comprise the normalized environmental data; and outputs of the artificial intelligence algorithm comprise environmental risks, consequences, and probabilities associated with at least one environmental event (906). Then the method can include modifying at least one planned project using the environmental risks, consequences, and probabilities associated with the at least one environmental event (908).

In some configurations, an additional input to the artificial intelligence algorithm is a list of categorized contaminants, wherein the list of categorized contaminants is generated by: receiving, at the computer system via web scraping, a list of water contaminants; stratifying, via the at least one processor, the list of water contaminants into categories based on commonalities, resulting in categories of contaminants; and classifying, via the at least one processor, the list of water contaminants into the categories of contaminants, resulting in the list of categorized contaminants. In such configurations, the environmental data comprises a list of water contaminants provided with a CAS (Chemical Abstracts Service) registration number of each chemical within the list of water contaminants. The water contaminant data can include both regulated and unregulated contaminants.

In some configurations, the artificial intelligence algorithm can include a neural network.

In some configurations, the at least one processor can generate a water toxicity score based at least in part on the environmental risks, consequences, and probabilities associated with at least one environmental event. In such configurations, the system can then transmit, from the computer system to a terminal computer in response to a request from the terminal computer, the water toxicity score.

Figure 10:
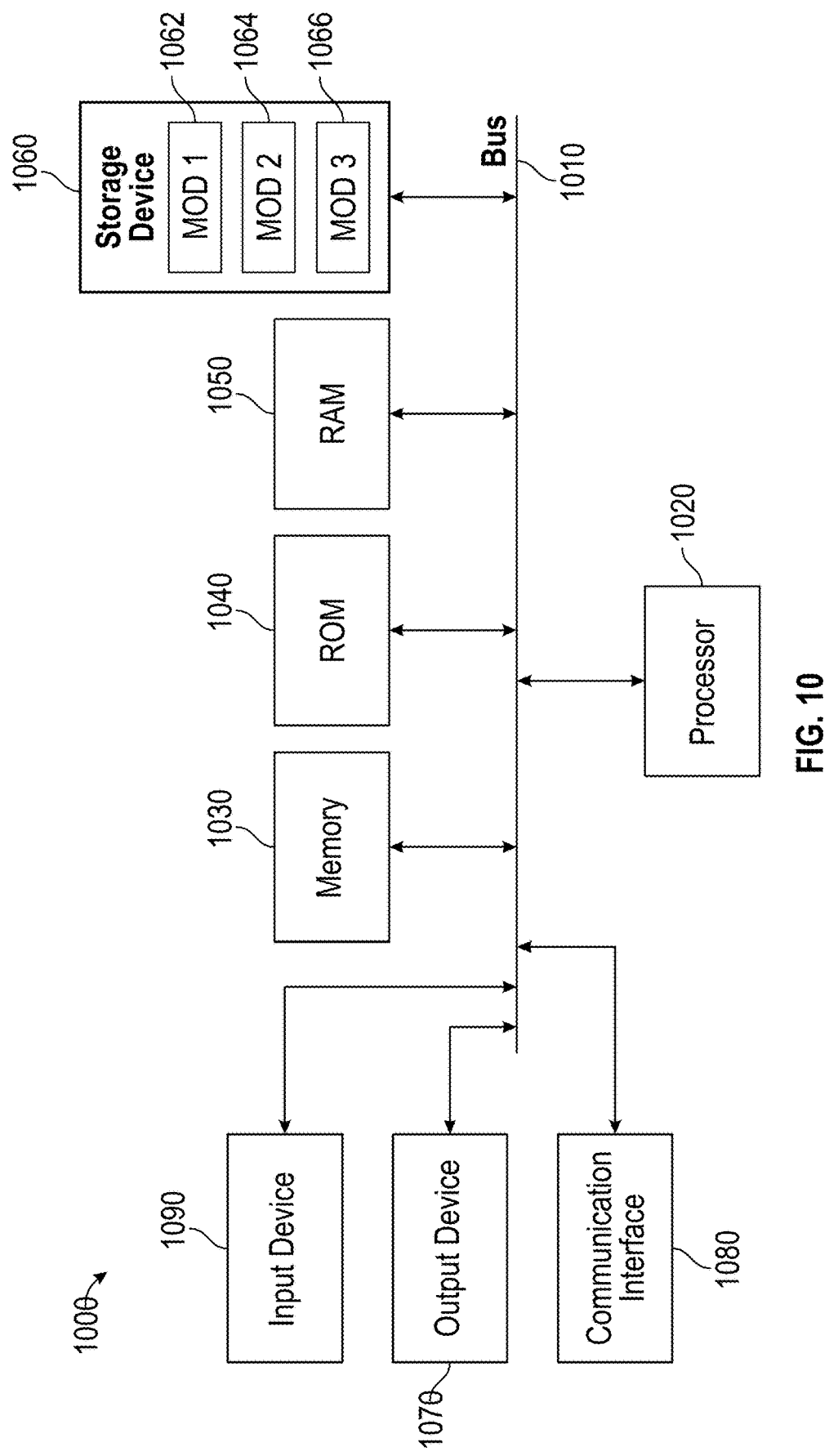
FIG. 10 illustrates an example computer system.

With reference to FIG. 10, an exemplary system includes a general-purpose computing device 1000, including a processing unit (CPU or processor) 1020 and a system bus 1010 that couples various system components including the system memory 1030 such as read-only memory (ROM) 1040 and random access memory (RAM) 1050 to the processor 1020. The system 1000 can include a cache of high-speed memory connected directly with, in close proximity to, or integrated as part of the processor 1020. The system 1000 copies data from the memory 1030 and/or the storage device 1060 to the cache for quick access by the processor 1020. In this way, the cache provides a performance boost that avoids processor 1020 delays while waiting for data. These and other modules can control or be configured to control the processor 1020 to perform various actions. Other system memory 1030 may be available for use as well. The memory 1030 can include multiple different types of memory with different performance characteristics. It can be appreciated that the disclosure may operate on a computing device 1000 with more than one processor 1020 or on a group or cluster of computing devices networked together to provide greater processing capability. The processor 1020 can include any general purpose processor and a hardware module or software module, such as module 1 1062, module 2 1064, and module 3 1066 stored in storage device 1060, configured to control the processor 1020 as well as a special-purpose processor where software instructions are incorporated into the actual processor design. The processor 1020 may essentially be a completely self-contained computing system, containing multiple cores or processors, a bus, memory controller, cache, etc. A multi-core processor may be symmetric or asymmetric.

The system bus 1010 may be any of several types of bus structures including a memory bus or memory controller, a peripheral bus, and a local bus using any of a variety of bus architectures. A basic input/output (BIOS) stored in ROM 1040 or the like, may provide the basic routine that helps to transfer information between elements within the computing device 1000, such as during start-up. The computing device 1000 further includes storage devices 1060 such as a hard disk drive, a magnetic disk drive, an optical disk drive, tape drive or the like. The storage device 1060 can include software modules 1062, 1064, 1066 for controlling the processor 1020. Other hardware or software modules are contemplated. The storage device 1060 is connected to the system bus 1010 by a drive interface. The drives and the associated computer-readable storage media provide non-volatile storage of computer-readable instructions, data structures, program modules and other data for the computing device 1000. In one aspect, a hardware module that performs a particular function includes the software component stored in a tangible computer-readable storage medium in connection with the necessary hardware components, such as the processor 1020, bus 1010, display 1070, and so forth, to carry out the function. In another aspect, the system can use a processor and computer-readable storage medium to store instructions which, when executed by the processor, cause the processor to perform a method or other specific actions. The basic components and appropriate variations are contemplated depending on the type of device, such as whether the device 1000 is a small, handheld computing device, a desktop computer, or a computer server.

Although the exemplary embodiment described herein employs the hard disk 1060, other types of computer-readable media which can store data that are accessible by a computer, such as magnetic cassettes, flash memory cards, digital versatile disks, cartridges, random access memories (RAMs) 1050, and read-only memory (ROM) 1040, may also be used in the exemplary operating environment. Tangible computer-readable storage media, computer-readable storage devices, or computer-readable memory devices, expressly exclude media such as transitory waves, energy, carrier signals, electromagnetic waves, and signals per se.

To enable user interaction with the computing device 1000, an input device 1090 represents any number of input mechanisms, such as a microphone for speech, a touch-sensitive screen for gesture or graphical input, keyboard, mouse, motion input, speech and so forth. An output device 1070 can also be one or more of a number of output mechanisms known to those of skill in the art. In some instances, multimodal systems enable a user to provide multiple types of input to communicate with the computing device 1000. The communications interface 1080 generally governs and manages the user input and system output. There is no restriction on operating on any particular hardware arrangement and therefore the basic features here may easily be substituted for improved hardware or firmware arrangements as they are developed.

Use of language such as "at least one of X, Y, and Z," "at least one of X, Y, or Z," "at least one or more of X, Y, and Z," "at least one or more of X, Y, or Z," "at least one or more of X, Y, and/or Z," or "at least one of X, Y, and/or Z," are intended to be inclusive of both a single item (e.g., just X, or just Y, or just Z) and multiple items (e.g., {X and Y}, {X and Z}, {Y and Z}, or {X, Y, and Z}). The phrase "at least one of" and similar phrases are not intended to convey a requirement that each possible item must be present, although each possible item may be present.

The various embodiments described above are provided by way of illustration only and should not be construed to limit the scope of the disclosure. Various modifications and changes may be made to the principles described herein without following the example embodiments and applications illustrated and described herein, and without departing from the spirit and scope of the disclosure.

Further aspects of the present disclosure are provided by the subject matter of the following clauses.

A method comprising: receiving, at a computer system from a plurality of sensors within a predefined geographic area, environmental data; normalizing, via at least one processor of the computer system, the environmental data, resulting in normalized environmental data; executing, via the at least one processor, an artificial intelligence algorithm, wherein: inputs to the artificial intelligence algorithm comprise the normalized environmental data; and outputs of the artificial intelligence algorithm comprise environmental risks, consequences, and probabilities associated with at least one environmental event; and modifying at least one planned project using the environmental risks, consequences, and probabilities associated with the at least one environmental event.

The method of any preceding clause, wherein an additional input to the artificial intelligence algorithm is a list of categorized contaminants; and wherein the list of categorized contaminants is generated by: receiving, at the computer system via web scraping, a list of water contaminants; stratifying, via the at least one processor, the list of water contaminants into categories based on commonalities, resulting in categories of contaminants; and classifying, via the at least one processor, the list of water contaminants into the categories of contaminants, resulting in the list of categorized contaminants.

The method of any preceding clause, wherein the environmental data comprises a list of water contaminants provided with a CAS (Chemical Abstracts Service) registration number of each chemical within the list of water contaminants.

The method of any preceding clause, the water contaminants comprising both regulated and unregulated contaminants.

The method of any preceding clause, wherein the artificial intelligence algorithm comprises a neural network.

The method of any preceding clause, further comprising: generating, via the at least one processor, a water toxicity score based at least in part on the environmental risks, consequences, and probabilities associated with at least one environmental event.

The method of any preceding clause, further comprising: transmitting, from the computer system to a terminal computer in response to a request from the terminal computer, the water toxicity score.

The method of any preceding clause, further comprising: developing a historical analysis using the normalized environmental data; developing, based on the historical analysis, a surface grid for the predefined geographic area; and generating, via the artificial intelligence algorithm, a grid-by-grid precipitation forecast for the predefined geographic area, where the inputs to the artificial intelligence algorithm further comprise the surface grid, and wherein the environmental risks, consequences, and probabilities generated by the artificial intelligence algorithm are based on the grid-by-grid precipitation forecast.

The method of any preceding clause, further comprising: identifying grid-specific variation characteristics for locations within the predefined geographic area, wherein the environmental risks, consequences, and probabilities generated by the artificial intelligence algorithm are based on the grid-specific variation characteristics.

The method of any preceding clause, wherein the artificial intelligence algorithm executes multiple iterations of a hydrological model for the predefined geographic area, resulting in future flow forecasts and a number of weather excursions.

The method of any preceding clause, wherein the artificial intelligence algorithm executes a Monte Carlo simulation of a hydrological model for the predefined geographic area, resulting in future flow forecasts and a number of weather excursions.

A method, comprising: developing, via at least one processor, a historical data analysis of water data for a predefined geographic area; developing, via the at least one processor, grid-specific variation characteristics of the predefined geographic area using the historical data analysis; generating, via the at least one processor, a future grid-by-grid precipitation forecast using the grid-specific variation characteristics; generating, via the at least one processor, future grid-specific variation characteristics using the future grid-by-grid precipitation forecast; generating, via the at least one processor, a future data analysis using the future grid-specific variation characteristics; and generating, via the at least one processor using the future data analysis, a ranked ordered list with risk zones within the predefined geographic area, the risk zones being portions of the predefined geographic area with a higher risk level for future hydrological events.

The method of any preceding clause, further comprising: generating future flow forecasts and weather excursions for the predefined geographic area using the future data analysis, wherein the future flow forecasts and the weather excursions are used to form the ranked ordered list.

The method of any preceding clause, wherein the forming of the future grid-by-grid precipitation forecast and the generating of the future grid-specific variation characteristics are performed by an artificial intelligence algorithm.

The method of any preceding clause, wherein the higher risk level is identified as a combination of costs for projected damage from the future hydrological events.

The method of any preceding clause, wherein the costs for projected damage comprises costs associated with human displacement, human death, and infrastructure repairs.

A system comprising: at least one processor; and a non-transitory computer-readable storage medium having instructions stored which, when executed by the at least one processor, cause the processor to perform operations comprising: receiving, from a plurality of sensors within a predefined geographic area, environmental data; normalizing the environmental data, resulting in normalized environmental data; executing an artificial intelligence algorithm, wherein: inputs to the artificial intelligence algorithm comprise the normalized environmental data; and outputs of the artificial intelligence algorithm comprise environmental risks, consequences, and probabilities associated with at least one environmental event; and modifying at least one planned project using the environmental risks, consequences, and probabilities associated with the at least one environmental event.

The system of any preceding clause, wherein an additional input to the artificial intelligence algorithm is a list of categorized contaminants; and wherein the list of categorized contaminants is generated by: receiving, via web scraping executed by the at least one processor, a list of water contaminants; stratifying, via the at least one processor, the list of water contaminants into categories based on commonalities, resulting in categories of contaminants; and classifying, via the at least one processor, the list of water contaminants into the categories of contaminants, resulting in the list of categorized contaminants.

The system of any preceding clause, wherein the environmental data comprises a list of water contaminants provided with a CAS (Chemical Abstracts Service) registration number of each chemical within the list of water contaminants.

The system of any preceding clause, the water contaminants comprising both regulated and unregulated contaminants.

The system of any preceding clause, wherein the artificial intelligence algorithm comprises a neural network.

The system of any preceding clause, the non-transitory computer-readable storage medium having additional instructions stored which, when executed by the at least one processor, cause the at least one processor to perform operations comprising: generating a water toxicity score based at least in part on the environmental risks, consequences, and probabilities associated with at least one environmental event.

The system of any preceding clause, the non-transitory computer-readable storage medium having additional instructions stored which, when executed by the at least one processor, cause the at least one processor to perform operations comprising: transmitting, to a terminal computer in response to a request from the terminal computer, the water toxicity score.

A non-transitory computer-readable storage medium having instructions stored which, when executed by at least one processor, cause the processor to perform operations comprising: receiving, from a plurality of sensors within a predefined geographic area, environmental data; normalizing the environmental data, resulting in normalized environmental data; executing an artificial intelligence algorithm, wherein: inputs to the artificial intelligence algorithm comprise the normalized environmental data; and outputs of the artificial intelligence algorithm comprise environmental risks, consequences, and probabilities associated with at least one environmental event; and modifying at least one planned project using the environmental risks, consequences, and probabilities associated with the at least one environmental event.

The non-transitory computer-readable storage medium of any preceding clause, wherein an additional input to the artificial intelligence algorithm is a list of categorized contaminants; and wherein the list of categorized contaminants is generated by: receiving, via web scraping executed by the at least one processor, a list of water contaminants; stratifying, via the at least one processor, the list of water contaminants into categories based on commonalities, resulting in categories of contaminants; and classifying, via the at least one processor, the list of water contaminants into the categories of contaminants, resulting in the list of categorized contaminants.

The non-transitory computer-readable storage medium of any preceding clause, wherein the environmental data comprises a list of water contaminants provided with a CAS (Chemical Abstracts Service) registration number of each chemical within the list of water contaminants.

The non-transitory computer-readable storage medium of any preceding clause, the water contaminants comprising both regulated and unregulated contaminants.

The non-transitory computer-readable storage medium of any preceding clause, wherein the artificial intelligence algorithm comprises a neural network.

The non-transitory computer-readable storage medium of any preceding clause, having additional instructions stored which, when executed by the at least one processor, cause the at least one processor to perform operations comprising: generating a water toxicity score based at least in part on the environmental risks, consequences, and probabilities associated with at least one environmental event.

We claim:

1. A method comprising:

receiving, at a computer system from a plurality of sensors within a predefined geographic area, environmental data;

normalizing, via at least one processor of the computer system, the environmental data, resulting in normalized environmental data;

training, via the at least one processor using training data, a neural network;

pruning the neural network to remove nodes which are not useful in providing accurate outputs, resulting in a modified neural network;

executing, via the at least one processor, an artificial intelligence algorithm based on the modified neural network, wherein:

inputs to the artificial intelligence algorithm comprise:

the normalized environmental data; and a list of categorized contaminants, wherein the list of categorized contaminants is generated by:

receiving, at the computer system via web scraping, a list of water contaminants;

stratifying, via the at least one processor, the list of water contaminants into categories based on commonalities, resulting in categories of contaminants; and classifying, via the at least one processor, the list of water contaminants into the categories of contaminants, resulting in the list of categorized contaminants; and outputs of the artificial intelligence algorithm comprise environmental risks, consequences, and probabilities associated with at least one environmental event; and modifying at least one planned project using the environmental risks, consequences, and probabilities associated with the at least one environmental event.

2. The method of claim 1, wherein the environmental data comprises a list of water contaminants provided with a CAS (Chemical Abstracts Service) registration number of each chemical within the list of water contaminants.

3. The method of claim 2, the water contaminants comprising both regulated and unregulated contaminants.

4. The method of claim 1, wherein the artificial intelligence algorithm comprises a neural network.

5. The method of claim 1, further comprising:

generating, via the at least one processor, a water toxicity score based at least in part on the environmental risks, consequences, and probabilities associated with at least one environmental event.

6. The method of claim 5, further comprising:

transmitting, from the computer system to a terminal computer in response to a request from the terminal computer, the water toxicity score.

7. A system comprising:

at least one processor; and a non-transitory computer-readable storage medium having instructions stored which, when executed by the at least one processor, cause the at least one processor to perform operations comprising:

receiving, from a plurality of sensors within a predefined geographic area, environmental data;

normalizing the environmental data, resulting in normalized environmental data;

training, using training data, a neural network;

pruning the neural network to remove nodes which are not useful in providing accurate outputs, resulting in a modified neural network;

executing an artificial intelligence algorithm based on the modified neural network, wherein:

inputs to the artificial intelligence algorithm comprise;

the normalized environmental data; and a list of categorized contaminants, wherein the list of categorized contaminants is generated by:

receiving, via web scraping executed by the at least one processor, a list of water contaminants;

stratifying, via the at least one processor, the list of water contaminants into categories based on commonalities, resulting in categories of contaminants; and classifying, via the at least one processor, the list of water contaminants into the categories of contaminants, resulting in the list of categorized contaminants; and outputs of the artificial intelligence algorithm comprise environmental risks, consequences, and probabilities associated with at least one environmental event; and modifying at least one planned project using the environmental risks, consequences, and probabilities associated with the at least one environmental event.

8. The system of claim 7, wherein the environmental data comprises a list of water contaminants provided with a CAS (Chemical Abstracts Service) registration number of each chemical within the list of water contaminants.

9. The system of claim 8, the water contaminants comprising both regulated and unregulated contaminants.

10. The system of claim 7, wherein the artificial intelligence algorithm comprises a neural network.

11. The system of claim 7, the non-transitory computer-readable storage medium having additional instructions stored which, when executed by the at least one processor, cause the at least one processor to perform operations comprising:

generating a water toxicity score based at least in part on the environmental risks, consequences, and probabilities associated with at least one environmental event.

12. The system of claim 11, the non-transitory computer-readable storage medium having additional instructions stored which, when executed by the at least one processor, cause the at least one processor to perform operations comprising:

transmitting, to a terminal computer in response to a request from the terminal computer, the water toxicity score.

13. A non-transitory computer-readable storage medium having instructions stored which, when executed by at least one processor, cause the at least one processor to perform operations comprising:

receiving, from a plurality of sensors within a predefined geographic area, environmental data;

normalizing the environmental data, resulting in normalized environmental data;

training, using training data, a neural network;

pruning the neural network to remove nodes which are not useful in providing accurate outputs, resulting in a modified neural network;

executing an artificial intelligence algorithm based on the modified neural network, wherein:

inputs to the artificial intelligence algorithm comprise:
the normalized environmental data; and
a list of categorized contaminants, wherein the list of
categorized contaminants is generated by:
receiving, via web scraping executed by the at
least one processor, a list of water contami-
nants;
stratifying, via the at least one processor, the list of
water contaminants into categories based on
commonalities, resulting in categories of con-
taminants; and
classifying, via the at least one processor, the list
of water contaminants into the categories of
contaminants, resulting in the list of categorized
contaminants; and
outputs of the artificial intelligence algorithm comprise
environmental risks, consequences, and probabilities
associated with at least one environmental event; and
modifying at least one planned project using the environ-
mental risks, consequences, and probabilities associ-
ated with the at least one environmental event.

14. The non-transitory computer-readable storage
medium of claim 13, wherein the environmental data com-
prises a list of water contaminants provided with a CAS
(Chemical Abstracts Service) registration number of each
chemical within the list of water contaminants.

15. The non-transitory computer-readable storage
medium of claim 14, the water contaminants comprising
both regulated and unregulated contaminants.

16. The non-transitory computer-readable storage
medium of claim 13, wherein the artificial intelligence
algorithm comprises a neural network.

17. The non-transitory computer-readable storage
medium of claim 13, having additional instructions stored
which, when executed by the at least one processor, cause
the at least one processor to perform operations comprising:
generating a water toxicity score based at least in part on
the environmental risks, consequences, and probabili-
ties associated with at least one environmental event.

* * * * *